United States Patent [19]

Philapitsch et al.

[11] Patent Number: 4,687,664

[45] Date of Patent: Aug. 18, 1987

[54] METHOD OF INACTIVATING REPRODUCIBLE PATHOGENS

[75] Inventors: Anton Philapitsch, Ebenfurt; Günter Wöber, Oberwaltersdorf; Johann Eibl; Otto Schwarz, both of Vienna, all of Austria

[73] Assignee: Immuno Aktiengesellschaft fur chemisch-medizinische Produkte, Vienna, Austria

[21] Appl. No.: 605,658

[22] Filed: Apr. 30, 1984

[30] Foreign Application Priority Data

May 2, 1983 [AT] Austria ............................. 1593/83
May 2, 1983 [AT] Austria ............................. 1592/83
May 2, 1983 [AT] Austria ............................. 1591/83
May 2, 1983 [AT] Austria ............................. 1590/83

[51] Int. Cl.$^4$ ............... A61K 39/395; C12N 9/00; C12N 7/04
[52] U.S. Cl. ............... 424/85; 424/101; 424/94.2; 424/94.3; 424/94.4; 514/2; 435/236; 435/185; 530/381; 530/383; 530/384
[58] Field of Search ............... 424/85, 101, 94; 435/236, 183; 530/380–387; 514/2

[56] References Cited

U.S. PATENT DOCUMENTS

| | | | |
|---|---|---|---|
| 3,100,737 | 11/1961 | Auerswald et al. | 424/101 |
| 3,203,865 | 8/1965 | Koehler et al. | 424/85 |
| 3,227,626 | 1/1966 | Baumgarten | 424/101 |
| 3,973,002 | 8/1976 | Hagan et al. | 424/101 |
| 4,297,344 | 10/1981 | Schwinn et al. | 424/85 |
| 4,379,085 | 4/1983 | Williams et al. | 424/101 |
| 4,388,232 | 6/1983 | Eibl et al. | 424/101 |
| 4,395,396 | 7/1983 | Eibl et al. | 424/101 |
| 4,405,603 | 9/1983 | Schwinn et al. | 424/101 |
| 4,440,679 | 4/1984 | Fernandes et al. | 424/85 |
| 4,470,968 | 9/1984 | Mitra et al. | 424/101 |
| 4,534,972 | 8/1985 | Lembach | 424/85 |

FOREIGN PATENT DOCUMENTS 0035204 9/1981 European Pat. Off. .

OTHER PUBLICATIONS

Miller-Anderson et al., Thrombosis Research, vol. 5, pp. 439-452, 1974.
Busby et al., J. Biol. Chem., vol. 256, pp. 12140–12147, 1981.
Fed. Proc., vol. 41, p. 763, Abstract 2877, 1982.
Austen and Rhymes; A Laboratory Manual of Blood Coagulation, pp. 50-52, 1975.
Suomela et al.; Vox Sang., vol. 33, pp. 37-50, 1977.
Odegard et al., Thrombosis Research, vol. 6, pp. 287-294, 1975.
Vogelaar et al., Vox Sang., vol. 26, pp. 118-127, 1974.
Rosen, American J. Hygiene, vol. 71, pp. 120-128, 1960.
Preston et al., J. Pathology and Bacteriology, vol. 78, pp. 209-216, 1959.
Deutsch et al., Science, vol. 170, pp. 1095-1096, 1970.
Friberger et al., Chromogenic Peptide Substrates: Chemistry and Clinical Usage, pp. 128-140, 1970.

*Primary Examiner*—Blondel Hazel
*Attorney, Agent, or Firm*—Burns, Doane, Swecker & Mathis

[57] ABSTRACT

There is described a method of inactivating reproducible pathogens in preparations containing plasmatic enzymes and proenzymes, activated or non-activated coagulation factors, such as Factors II, V, VII, VIII, IX, X, XIII, "FEIBA", prothrombin complex preparations, plasmatic inhibitors, immunoglobulins or other blood products, such as fibronectin and fibrinogen. In order to break and overcome the protective effect of proteins on pathogens by simultaneously preserving the biological activity and the molecular integrity of the proteins, the preparation is adjusted to a salt concentration of more than 0.5 molar by the addition of ammonium sulfate and is thermally treated, whereupon the ammonium sulfate is removed from the preparation.

15 Claims, No Drawings

METHOD OF INACTIVATING REPRODUCIBLE PATHOGENS

The invention relates to a method of inactivating reproducible pathogens in preparations containing plasmatic enzymes and proenzymes, activated or non-activated coagulation factors, such as Factors II, V, VII, VIII, IX, X, XIII, "FEIBA", prothrombin complex preparations, plasmatic inhibitors, immunoglobulins or other blood products, such as fibronectin and fibroinogen.

From the published European Pat. No. 0,018,561 it is known to stabilize coagulation factors containing preparations, which are practically free of fibrinogen, against heat influence by adding to the solution of coagulation factors an amino acid and a mono- or oligo-saccharide or a sugar alcohol. After such as treatment, the preparation may be heated at 60° C. for 10 hours, wherein it is known that such a treatment causes an inactivation of hepatitis viruses in human albumin. The known method has the disadvantage that the yield of coagulation factors is unsatisfactory. Furthermore, the method has not been tested with respect to model viruses so that the inactivation potential of this stablizing treatment on various pathogens is not known.

According to the published European Pat. No. 0,052,827 a method of producing a preparation of coagulation Factors II and/or VII has, furthermore, become known, which is deemed to be hepatitis safe; the method consists in heating the preparation in the presence of an amino acid, a saccharide or sugar alcohols and a chelating agent, such as a salt of ethylenediamino tetraacetic acid.

According to the published European Pat. No. 0,053,338, in a method for the production of a preparation containing blood coagulation Factors IX and/or X and considered hepatitis safe, the preparation is heated in the presence of an amino acid, a saccharide or sugar alcohol and Ca ions, wherein the Ca ions are said to have a stabilizing effect against thermal inactivation on Factors IX and X.

In the published European Pat. No. 0,035,204 a method of preparing a protein composition is, furthermore, described, which method consists in mixing the composition with a polyol and heating the mixture for a time sufficient to pasteurize the protein composition. A modification of this method is described in the published European Pat. No. 0,065,256, wherein a solution of plasminogen, which, if desired, contains an amino acid, a saccharide or a sugar alcohol, is heated in the presence of a proteinase inhibitor. Also with this method, the inactivation potential of the treatment is not known and the yield is unsatisfactory.

A further method of the prior art is described in U.S. Pat. No. 3,227,626, in which a plasminogen solution is heated at 60° C. for 10 hours in the presence of lysin in order to sterilize the preparation. An activity with respect to a certain virus spectrum cannot be taken from this document, either.

In a further piece of literature, i.e. Fed. Proc. Vol. 41, 1982, Abstract 2877, page 763, it is said that a $C_1$-inactivator ($C_1$-INA) containing concentrate is advantageously used in therapy if it is heated at 60° C. for 10 hours in the presence of potassium or ammonium citrate, which treatment reduces the risk of a hepatitis transmission.

A similar method has become known for the Journal of Biological Chemistry, Vol. 256, 1981, No. 23, page 12140, for the stabilization of an antithrombin III preparation.

From German Offenlegungsschrift No. 31 02 217 it is, furthermore, known to admix a plasminogen preparation with a physiologically compatible anorganic salt, lysin, phenylmethane sulfonylfluoride, aprotinin or soybean-trypsin-inhibitor, yet, with this known method, the added salts or inhibitors are not removed, but remain in the end product, thus reducing the activity of the preparations and their compatibility.

All these methods have the disadvantage in common that the inactivation potential of this treatment is not known and the yields are not satisfactory.

The invention aims at avoiding the difficulties described. It is based on the new findings that the inactivation of pathogens in biological and pharmaceutical media is inhibited by proteins contained in the preparations. The invention has as its object to break and overcome this protective effect of proteins on pathogens—by stimultaneously preserving the biological activity and the molecular integrity of the proteins—in order to make available safe blood product preparations. The measures pertaining to the prior art do not have this effect. On the contrary, some of them have an additional stabilizing effect on pathogens.

With a method of the initially defined kind, the invention consists in that the preparation is adjusted to a salt concentration of more than 0.5 molar by the addition of ammonium sulfate (AMS) and is thermally treated, whereupon the ammonium sulfate is removed from the preparation.

Suitably, a preparation with a protein content of 0.001 to 30% is used.

Advantageously, a 2 to 4 molar ammonium sulfate concentration is used for the thermal treatment of the preparation.

According to a preferred embodiment, a protein and AMS containing precipitate is recovered from the preparation by the addition of ammonium sulfate, which precipitate is subjected to thermal treatment.

Furthermore, the ammonium sulfate containing preparation may be lyophilized, with the lyophilisate being exposed to thermal treatment, whereupon a solution is reconstituted by the addition of an aqueous solvent to the lyophilisate and the salt is removed therefrom.

The thermal treatment of the solution takes place over a period of from 1 second to 100 hours and at a temperature of from 40° C. to 121° C. Preferably, the thermal treatment is carried out as a shock treatment.

The pH of the preparation during treatment is maintained within a range of from 5 to 11, preferably of from 6.5 to 8.5.

Suitably, protein stabilizing substances, such as glycine and/or antimicrobial substances, such as caprylate, are added to the preparation prior to thermal treatment.

According to the invention, the removal of ammonium sulfate from the preparation suitably is effected with the help of semi-permeable membranes.

The invention is also related to a preparation containing plasmatic enzymes and proenzymes, activated or non-activated coagulation factors, such as Factors II, V, VII, VIII, IX, X, XIII, "FEIBA", prothrombin complex preparations, plasmatic inhibitors, immunoglobulins or other blood products, such as fibronectin and fibrinogen, which is obtained by treatment of the same with ammonium sulfate at a concentration of more than 0.5 molar as well as by thermal treatment and removal of the salt from the preparation and by rendering its stable, in particular by lyophilization.

As already pointed out, one of the principles on which the invention is based is the finding that the protective effect of proteins on pathogens is neutralized by ammonium sulfate and thermal treatment. This fact is going to be illustrated in the following model assays by way of different viruses.

ASSAY 1

Poliomyelitis virus type I was introduced into an isotonic saline solution on the one hand and into a 5% plasma protein solution on the other hand. The two solutions, admixed with polio virus, were heated at 45° C. for 10 hours and subjected to a virus titer determination. The values in the following Table are decadic logarithms of $TCID_{50}$ per 0.1 ml, $TCID_{50}$ meaning that 50% of the cell culture preparations exhibited a cytopathic effect.

|  | Virus titer after 10 hours of heating at 45° C. |
|---|---|
| Virus in isotonic saline solution | 3.9 |
| Virus in plasma protein solution | 7.8 |

The assay was repeated with the same virus, yet the two solutions are admixed with ammonium sulfate (AMS) approximately until salt saturation (0.7 g ammonium sulfate per ml) prior to heating, which resulted in a pH of 7.3. After 10 hours of heating at 45° C., the virus titer was determined as follows.

|  | Virus titer after 10 hours of heating at 45° C. |
|---|---|
| Virus in AMS containing isotonic saline solution | 4.0 |
| Virus in AMS containing plasma protein solution | <3 |

ASSAY 2

Poliomyelitis virus type I, rotavirus and Coxsackie virus were each added to a plasma protein solution with a content of 54 mg protein ml. To every 10 ml of these plasma protein solutions admixed with viruses were added 7 g ammonium sulfate and the pH was adjusted to 7.0.

In parallel experiments the virus and ammonium sulfate containing solutions were maintained once at 4° C. for 10 hours and once at 60° C. for 10 hours. Subsequently, the salt was removed from the samples by dialysis and a virus titer determination was done. The values indicated in the following Table are decadic logarithms of $TCID_{50}/0.1$ ml.

|  | Virus titer | |
|---|---|---|
|  | 10 h/4° C. | 10 h/60° C. |
| Poliomyelitis virus type I + AMS in plasma protein solution | 7.2 | <1 |
| Rotavirus + AMS in plasma protein solution | 9.0 | <1 |
| Coxsackie virus + AMS in plasma protein solution | 9.0 | <1 |

The method according to the invention will now be explained in more detail in examples by way of production methods of different preparations containing blood products, wherein, in order to illustrate the inactivation effect of the measures to be applied according to the invention, viruses are deliberately added at a certain stage of the fractionation process.

EXAMPLE 1

46 l fresh frozen plasma were thawed at 0° C. to +4° C. The cryoprecipitate formed was separated by centrifugation and dissolved in 960 ml of a 0.1% trisodium-citrate solution at 37° C. This Factor VIII containing dissolved cryoprecipitate was adjusted to a pH of 6.0 to 6.8 according to the method described in U.S. Pat. No. 3,973,002 to form a precipitate, which was separated by centrifugation and discarded. This solution was adjusted to a Factor VIII content of 20 units/ml and admixed with poliomyelitis virus type I; then, ammonium sulfate (AMS) was added in an amount of 0.7 g/ml and the pH was adjusted to 7.3. Thereafter, the preparation was divided into four portions for treatments at +4° C., 50° C., 55° C. and 60° C. for 10 hours. Subsequently, the virus titer was determined.

The results will be apparent from the following Table.

|  | Treatment temperature | Virus titer |
|---|---|---|
| Factor VIII preparation + virus + AMS | 4° C. | 8 |
| Factor VIII preparation + virus + AMS | 50° C. | <3 |
| Factor VIII preparation + virus + AMS | 55° C. | <3 |
| Factor VIII preparation + virus + AMS | 60° C. | <3 |

It is evident that the virus titer was reduced to less than $10^3$ on account of the saline and thermal treatment according to the invention.

EXAMPLE 2

To a Factor VIII preparation prepared according to Example 1, yet with a protein content of 7 mg/ml (2 U F. VIII/ml), poliomyelitis virus type I was admixed, then ammonium sulfate in an amount of 0.8 g/ml was added, and the resulting solution was thermally treated during periods of 2 minutes, 6 minutes, 20 minutes, 3 hours and 10 hours at 60° C.

A parallel assay was carried out, in which, however, sodium caprylate in an amount of 16 mmol/g protein was added to the mixture prior to the addition of ammonium sulfate. The results will be apparent from the following Table.

|  | Duration of thermal treatment at 60° C. | Virus titer of Factor VIII preparation + AMS | |
|---|---|---|---|
|  |  | without caprylate | with caprylate |
| Initial value | — | 6.8 | 6.0 |
|  | 2 minutes | 6.3 | 6.8 |
|  | 6 minutes | 6.2 | 5.8 |
|  | 20 minutes | 5.7 | <2.5 |
|  | 60 minutes | 4.5 | <2.5 |
|  | 3 hours | <2 | <2.5 |
|  | 10 hours | <2 | <2.5 |

It is evident that, without addition of caprylate, a pronounced reduction of virus titer occurs after 3 hours; with the addition of caprylate, this effect occurs after only 20 minutes.

In the following examples the further important effect of the invention, i.e. the preservation of the biological activity of Factor VIII containing preparations after saline and thermal treatment with varying salt concentrations, will be illustrated.

EXAMPLE 3

10 ml each of the virus-containing Factor VIII preparation prepared in the manner described and containing 2 units of Factor VIII/ml were admixed with 6.4 g, 8.0 g, 9.6 g ammonium sulfate. The pH was adjusted to pH 7.0 and the mixtures were stirred until the ammonium sulfate had dissolved completely or a saturation of ammonium sulfate had been reached. The solutions were placed into a water bath and heated at 60° C. for 10 hours. Control preparations with the same contents of Factor VIII units and equal ammonium sulfate contents were not exposed to thermal treatment. All the samples were subjected to dialysis against NaCl-Na citrate solutions at 6 g/l each in order to eliminate the ammonium sulfate with the help of a semi-premeable membrane. Subsequently, a Factor VIII activity determination (2-step assay method in "A Laboratory Manual of Blood Coagulation", D. E. G. Austen, I. L. Rhymes; Blackwell Scientific Publications 1975) and a virus titer determination were carried out at all the samples. The activities of the thermally treated samples were compared with the unheated ammonium sulfate admixed controls and expressed in % residual activity Factor VIII. The results are indicated in the following Table.

| Factor VIII preparations with | % Residual activity Factor VIII | virus titer |
| --- | --- | --- |
| 6.4 g AMS/10 ml | 61 | <2 |
| 8.0 g AMS/10 ml | 53 | <2 |
| 9.6 g AMS/10 ml | 87 | <2 |
| Control samples | | 6.8 |

No virus activity could be detected in the thermally treated samples mixed with AMS.

EXAMPLE 4

In the following Example the effect of the AMS-thermal treatment according to the invention with respect to different protein concentrations is shown, wherein it is evident that the effect is achieved over an extremely wide concentration range.

A Factor VIII containing preparation was prepared as described. The protein content of this Factor VIII preparation was adjusted to 1 mg protein/ml and 3 mg protein/ml by a 0.1% trisodiumcitrate solution. In order to produce a Factor VIII containing preparation with 100 mg protein/ml, the described Factor VIII containing preparation was admixed with a highly concentrated plasma protein solution (about 20% protein solution) so that a Factor VIII preparation with 100 mg protein/ml resulted. Thereafter, poliomyelitis virus was added as described.

10 ml each of the Factor VIII containing protein solution with 1 mg, 3 mg and 100 mg protein/ml, respectively, were admixed with 8 g ammonium sulfate. After dissolution of the salt, the mixtures were adjusted to a pH of 7.0 and heated at 60° C. for 10 hours. Subsequently, the ammonium sulfate was eliminated by dialysis and the residual activity of Factor VIII of the samples as compared to untreated samples were determined.

| Factor VIII + AMS 10 hours at 60° C. in a | % Residual activity Factor VIII | Virus titer |
| --- | --- | --- |
| 0.1% protein solution | 13 | <3 |
| 0.3% protein solution | 30 | <3 |
| 10.0% protein solution | 55 | <3 |

EXAMPLE 5

In this Example the influence of thermal treatments at different temperatures after the addition of ammonium sulfate to Factor VIII preparations is illustrated.

10 ml each of the virus containing Factor VIII preparation prepared according to Example 1 and containing 2 U/ml were admixed with 7.2 g ammonium sulfate. After the ammonium sulfate had dissolved, the pH was adjusted to 6.5 and the mixtures were heated at varying temperatures for 10 hours; the elimination of ammonium sulfate and the Factor VIII activity determination were effected as in Example 4.

The activities of the thermally treated ammonium sulfate samples were compared with the activity of the untreated sample and expressed in % of residual activity. The results are indicated in the following Table.

| Treatment at | % Residual activity F. VIII | Virus titer |
| --- | --- | --- |
| 45° C. | 100 | <2 |
| 50° C. | 100 | <2 |
| 55° C. | 90 | <2 |
| 60° C. | 67 | <2 |
| 62° C. | 67 | <2 |
| 66° C. | 58 | <2 |

It is evident that the residual activity is preserved to a great extent even at a temperature of above 60° C. and that the virus is inactivated.

EXAMPLE 6

10 ml of a Factor VIII and virus containing preparation with 2 U Factor VIII/ml were admixed with 8 g ammonium sulfate. After dissolution of the ammonium sulfate, the pH was adjusted to 7.0 and the mixture was heated at 90° C. for 3 minutes. Subsequently, the ammonium sulfate was eliminated by dialysis and the thermally treated preparation was subjected to Factor VIII determination. The activity was compared with the activity of the untreated Factor VIII containing preparation and expressed in % residual activity.

Thus, it was found out that even at a relatively high temperature of 90° C., the residual activity remained preserved by 35%, the virus losing its activity. The virus titer is <3.

EXAMPLE 7

In this Example, the pH dependency within the scope of the method according to the invention is illustrated.

10 ml each of a Factor VIII and virus containing preparation with 7 mg/ml protein and 2 U Factor VIII/ml were admixed with 7.2 g of ammonium sulfate. After dissolution of the salt, the pH values of the individual mixtures were adjusted as follows: pH 6.5, 7.0, 7.5, 8.0, 8.5, 9.0, 10.0. The thus pH-adjusted samples were heated at 60° C. for 10 hours. Subsequently, the elimination of ammonium sulfate by dialysis, the determination of Factor VIII, expressed as % residual activity of untreated Factor VIII containing sample, and the virus titer determination were carried out.

|  | pH 6.5 | 7.0 | 7.5 | 8.0 | 8.5 | 9.0 | 10.0 |
|---|---|---|---|---|---|---|---|
| Virus titer | <2 | <2 | <2 | <2 | <2 | <2 | <2 |
| % Residual act. Factor VIII after 10 h at 60° C. with AMS | 65 | 60 | 65 | 55 | 60 | 35 | 25 |

In the following Example, the influence of the addition of glycine to a Factor VIII containing fraction is illustrated.

EXAMPLE 8

37 l fresh frozen plasma were thawed at 0° C. to +4° C. The Factor VIII containing cryoprecipitate formed was separated by centrifugation and dissolved with 400 ml of a 0.1% trisodium citrate solution at 37° C. The solution contained 66 mg protein and 22 U Factor VIII/ml. To the solution was added a poliomyelitis virus type I.

10 ml each of this Factor VIII and virus containing protein solution were
(a) admixed with 8 g ammonium sulfate, the pH was adjusted to 7 and the solution was heated at 60° C. for 10 hours;
(b) admixed with 0.05 g glycine and 8 g ammonium sulfate, the pH was adjusted to 7 and the solution was heated at 60° C. for 10 hours;
(c) admixed with 0.1 g glycine and 8 g ammonium sulfate, the pH was adjusted to 7 and the solution was heated at 60° C. for 10 hours;
(d) admixed with 0.5 g glycine and 8 g ammonium sulfate, the pH was adjusted to 7 and the solution was heated at 60° C. for 10 hours.

Subsequently, the ammonium sulfate was eliminated by dialysis and the % residual activity Factor VIII of the thermally treated samples as compared with the untreated samples was determined, and so was the virus titer. The results are summarized in the following Table.

|  | Glycine content of Factor VIII preparations | | | |
|---|---|---|---|---|
|  | without glycine | 0.5% glycine | 1% glycine | 5% clycine |
| Virus titer | <2 | <2 | <2 | <2 |
| % Residual act. F. VIII after AMS - 10 h 60° C. | 15 | 23 | 39 | 69 |

EXAMPLE 9

2 ml of a Factor VIII preparation produced in the described manner and having a protein content of 38 mg and 29.5 U Factor VIII/ml were admixed with 1.6 g ammonium sulfate, and the pH was adjusted to 7.0 and the mixture of precipitate and solution was freeze-dried. The lyophilized sample was heated at 60° C. for 10 hours, reconstituted with water, subjected to dialysis, and finally a Factor VIII activity determination was done. The Factor VIII residual activity was 34% as compared to a thermally untreated control.

EXAMPLE 10

Fresh frozen human citrated plasma was thawed, the cryoprecipitate forming was separated. To the cryosupernatant DEAE-Sephadex was added, the FEIB-(Factor-Eight-Inhibitor-Bypass)-activity being generated according to German Offenlegungsschrift No. 31 27 318 during a contact time of 12 hours. The coagulation factors including FEIBA are then eluted from DEAE-Sephadex by a buffer. After a lyophilization step, a bulk material is available. Of this powder, 312 mg are dissolved by 10 ml H$_2$O. This solution contains 20 mg protein, 24 U FEIBA and 28 U Factor VII/ml. To illustrate the inactivation effect of the measures to be applied according to the invention, a virus, i.e., a virus of poliomyelitis type I, was then deliberately added to this product. Thereafter, ammonium sulfate (AMS) in an amount of 0.8 g/ml was added to a sample of the virus admixed product, while a control sample remained salt-free. Both samples were adjusted to pH 7. The saline sample was heated at 60° C. for 10 hours and subsequently the virus titer was determined with both samples. The results are shown in the following Table.

|  | Virus titer | |
|---|---|---|
|  | Sample after AMS-thermal inactivation | Untreated control sample (+4° C.) |
| Preparation containing Factors II, VII, IX, X, FEIBA | <2.5 | 7.1 |

The combined AMS-thermal treatment according to the invention not only causes a reliable inactivation of pathogens, such as viruses, but a likewisely important effect is the preservation of the biological activity and of the molecular integrity of proteins. In order to prove this, the coagulation factor FEIBA preparation described above was subjected to activity determination prior and after AMS-thermal treatment, AMS having been eliminated by dialysis. The activity determination was done according to the methods described in the German Offenlegungsschrift No. 31 27 318 mentioned. The results can be taken from the following Table.

|  | F. II | F. VII | F. IX | F. X | FEIBA |
|---|---|---|---|---|---|
| Residual activity after AMS-thermal treatment 0.8 g AMS/ml 10 h 60° C. | 61 | 43 | 41 | 27 | 39 |

EXAMPLE 11

According to the method described in Vox Sang. 33: pp. 37 to 50 (1977), coagulation Factors II, IX and X were obtained from human plasma via adsorption at DEAE-Sephadex, washing of the anion exchanger and elution of the partial prothrombin complex. The eluate was subjected to a dialysis and lyophilization process. Of this bulk powder, 467 mg were dissolved by 10 ml H$_2$O. This solution contained 35 mg protein, 70 U Factor II, 52 U Factor IX and 61 U Factor X/ml, thus constituting a preparation of a partial prothrombin complex.

As described above, poliomyelitis virus type I was added to the preparation, and the preparation with AMS was subjected to a 10-hour thermal treatment at 60° C. Subsequently, the virus titer determination was done, and after dialysis the determination of the activity of the coagulation factors was carried out. The results are indicated in the following Table.

| | Virus titer | |
|---|---|---|
| | Sample after AMS-thermal inactivation | Untreated control sample (+4° C.) |
| Preparation containing partial prothrombin complex | <2.5 | 6.6 |

| | % Residual activity after AMS-thermal treatment Acitivity Factor | | |
|---|---|---|---|
| | II | IX | X |
| 0.8 g AMS/ml, 10 h 60° C. | 66 | 39 | 28 |

EXAMPLE 12

According to the method described in U.S. Pat. No. 4,388,232, a preparation containing coagulation factor VII was prepared from human citrated plasma. After separation of the cryoprecipitate and DEAE-Sephadex treatment, Factor VII was adsorbed on Al(OH)$_3$. Al(OH)$_3$ was subjected to a washing process and a Factor VII elution process at an elevated ionic strength. The Factor VII containing eluate was dialyzed and lyophilized. 192 mg of the bulk powder were dissolved in 10 ml H$_2$O. This solution contained 10.3 mg protein and 21 U Factor VII/ml. As described above, also in this case, poliomyelitis virus type I was deliberately added and the preparation with AMS was subjected to a 10 hour thermal treatment at 60° C. Subsequently, the virus titer determination and, after dialysis, the determination of the activity of the coagulation factors were done. The results are summarized in the following Table.

| | Virus titer | |
|---|---|---|
| | Sample after AMS-thermal inactivation | Untreated Control sample (+4° C.) |
| Preparation containing Factor VII | <3 | 7.5 |
| Activity | Factor VII | |
| % Residual activity after AMS-thermal treatment 0.8 g AMS/ml 10 h 60° C. | 58 | |

EXAMPLE 13

An antithrombin III preparation was prepared according to the method described in "Thrombosis Research 5, p. 439 (1979)" from human plasma by affinity chromatography via heparin agarose and lyophilized. 530 mg of this antithrombin III containing bulk material was dissolved in 10 ml water. This solution contained 26 mg protein and 25 U antithrombin III per ml.

The preparation was then admixed with poliomyelitis virus type I. Thereafter, ammonium sulfate in an amount of 0.8 g/ml was added to the preparation and the pH was adjusted to 7. Then the sample was heated at 60° C. for 10 hours, the salt was removed by dialysis and the virus titer and the activity of antithrombin III in the preparation were amidolytically measured. The determination technique is described in Thrombosis Research 6, p. 287, 1975. The residual activity is expressed in % relative to an untreated sample.

In the following Table the virus titers are expressed in decadic logarithms of TCID$_{50}$/0.1 ml; the residual activity is indicated in percent.

| | Virus titer | | Residual activity % |
|---|---|---|---|
| | without AMS | 10 h/60° C. with AMS | |
| Antithrombin III preparation | 6.9 | <2.5 | 71 |

EXAMPLE 14

A C$_1$-esterase inhibitor preparation was obtained according to the method described in Vox. Sang. 26, p. 118 (1974) from human plasma via anionic exchanger (DEAE-Sephadex) by adsorption and subsequent elution. After a salt precipitation to separate undesired proteins, the purified C$_1$-inhibitor preparation was freeze-dried. 650 mg of the C$_1$-inhibitor containing bulk material was dissolved in 10 ml water. 1 ml of this solution contained 49 mg protein and 60 U C$_1$-INA.

The solution was inoculated with poliomyelitis virus type I and then treated in the manner according to the invention by adding 0.8 g ammonium sulfate/ml, adjusting the pH to 7 and heating the sample at 60° C. for 10 hours. After removal of the ammonium sulfate by means of dialysis, a virus titer determination was carried out and the residual activity of C$_1$-inhibitor was determined with chromogenic substrate according to the method described in "Mikrozirkulation und Prostaglandinstoffwechsel", Proceedings of the 25th Congress of the Deutschen Arbeitsgemeinschaft für Blutgerinnungsforschung in München, February 1981, p. 221, Schattauer-Verlag, 1981.

In the following Table the virus titer values, indicated in decadic logarithms of TCID$_{50}$/0.1 ml, and the residual activity in % relative to an untreated sample are shown.

| | Virus titer 10 h/60° C. | | Residual activity % |
|---|---|---|---|
| | without AMS | with AMS | |
| C$_1$-esterase inhibitor preparation | 6.9 | <2.5 | 85 |

EXAMPLE 15

In this Example the influence of the treatment according to the invention is demonstrated by way of a plasma preparation. Plasma was admixed with poliomyelitis virus type I, ammonium sulfate was added in an amount of 0.8 g/ml, the pH was adjusted to 7 and the sample was subjected to thermal treatments at 60° C., 65° C. and 75° C. for 10 hours. Subsequently, the ammonium sulfate was eliminated by dialysis, the virus titer was determined and the trypsin inhibition was measured.

In the following Table the virus titer values are indicated in decadic logarithms of TCID$_{50}$/0.1 ml and the trypsin-inhibiting activity of plasma is expressed as % residual activity with respect to an untreated control.

| | Control | Virus titer 10 h | | | % Residual activity of trypsin inhibition | | |
|---|---|---|---|---|---|---|---|
| | | 60° C. | 65° C. | 75° C. | 60° C. | 65° C. | 75° C. |
| Plasma + AMS | | <2.5 | <2.5 | <2.5 | 62 | 62 | 53 |

-continued

|  | Virus titer 10 h | | | % Residual activity of trypsin inhibition | | |
|---|---|---|---|---|---|---|
|  | Control | 60° C. | 65° C. | 75° C. | 60° C. | 65° C. | 75° C. |
| Plasma without AMS | 7 | | | | | | |

The method for determining the residual activity consists in that 86.4 mg trypsin (pancreas protease Merck Art. No. 8367) are dissolved in 100 ml $10^{-3}$n HCl. This trypsin solution is mixed with the sample to be determined, the trypsin inhibitors present in the plasma neutralizing the added trypsin. Non-neutralized trypsin is measured amidolytically with chromogenic substrate Bz-Ileu-Glu-Gly-Arg-pNA. The remaining trypsin amount is related to a trypsin blank value, with which no addition of sample occurred. It constitutes an indirect measure for the trypsin inhibitors.

EXAMPLE 16

An immunoglobulin preparation was obtained from human plasma by the alcohol fractionation method according to Cohn (Cohn Fraction II). The solution contained 160 mg protein with a portion of 97.3% gammaglobulin and 2.7% $=,\beta$ globulins, 22.5 mg glycin and 3 mg NaCl per ml.

The solution was then admixed with poliomyelitis virus type I. Then, 0.8 g ammonium sulfate/ml were added to the sample, the pH was adjusted to 7 and the preparation was heated to 60° C. for 10 hours. Subsequently, the ammonium sulfate was eliminated by dialysis and the virus titer was determined.

The results as compared to an untreated sample will be apparent from the following Table, the indicated values being the decadic logarithms of $TCID_{50}/0.1$ ml.

|  | Virus titer | |
|---|---|---|
|  | 10 h/4° C. without AMS | 10 h/60° C. with AMS |
| Immunoglobulin preparation | 5.7 | <2.5 |

In order to be able to realize possible changes at the immunoglobulin preparations treated according to the invention, an electrophoretic separation of the globulins was carried out with the sample treated with ammonium sulfate and with heat, on a cellulose-acetate membrane at a pH of 8.6 and an ionic strength of 0.075. Such an electrophoretic investigation is described in U.S. Pat. No. 4,395,396.

The results of the electrophoretic separation will be apparent from the following Table.

|  | % Protein | |
|---|---|---|
|  | $\alpha,\beta$-globulins | $\gamma$-globulins |
| Control without thermal treatment | 2.7 | 97.3 |
| Sample with AMS 10 h/60° C. | 2.9 | 97.1 |

It is, thus, to be seen that no changes have occurred as compared to the untreated sample, i.e. that the proteins have remained unchanged with respect to their molecular integrity and mobility.

Furthermore, the preparation treated with ammonium sulfate and heat according to the invention was subjected to an antibody test against measles, rubella and pertussis in order to prove that the effects of the antibodies remain preserved during the AMS heat treatment. Hemoagglutination inhibition tests and an agglutination titer test were carried out according to the method described in American Journal of Hygiene 71, p. 120 (1960); Journal Path. and Bact. 78 (1959); R. Trian in Recherches Immunologiques 1965 Inst. Merieux, in order to determine the antibodies against measles, rubella and pertussis, respectively. With this method the content of virus neutralizing antibodies was determined. Under particular conditions, viruses provoke an aggregation of erythrocytes. These agglutinating properties of virus antigens will be lost by reaction with specific antibodies. In order to quantify this procedure, the sample was diluted, each dilution being incubated with the same amount of virus antigen. The end point is reached when the antibodies of the sample have bound all the antigens present and no agglutination with erythrocytes occurs. The highest dilution at which this reaction occurs is the end point, as indicated in the following Table in the case of pertussis and rubella. With measles antibodies, the dilution step is still compared with that of the International WHO standard, being expressed as an International Unit.

|  | Antibodies | | |
|---|---|---|---|
|  | Measles IU/ml | Pertussis Dilution step | Rubella Dilution step |
| Control | 12 | 1:142 | 1:168 |
| Immunoglobulin AMS 10 h 60° C. | 12 | 1:142 | 1:200 |

EXAMPLE 17

A plasminogen preparation was prepared according to the method described by D. G. Deutsch and E. T. Mertz in Science 170, 1095 (1970). 50 ml lysin-Sepharose were equilibrated in a column with 0.1M phosphate, pH 7.4, 340 ml plasma were diluted with water to 640 ml and the column was packed with this solution. After elimination of accompanying proteins by washing with a 0.3M phosphate solution (pH 7.4), the plasminogen was eluted with 0.2M 6-aminocaproic acid (pH 7.4). The 6-aminocaproic acid was removed by dialysis or by gel filtration over Sephadex G-25 and the plasminogen containing solution was freeze-dried.

230 mg of this bulk powder were dissolved in 10 ml water. This solution contained 271 Casein units of plasminogen and 13 mg protein per ml.

The preparation was admixed with poliomyelitis virus type I as described in the preceding Example, then 0.8 g ammonium sulfate/ml were added, the pH was adjusted to 7 and the preparation was heated at 60° C. for 10 hours. Subsequently, ammonium sulfate was removed by dialysis and the virus titer as well as the activity of plasminogen were determined with urokinase and a chromogenic substrate (H-D-Val-Leu-Lys-pNA) according to the technique described in "Chromogenic Peptide Substrates: Chemistry and Clinical Usage", Edt. M. F. Scully, V. V. Kakker, p. 128 (1979), publ. by Churchill Livingstone.

In the following Table the virus titer and the residual activity as compared to untreated control samples are illustrated, the indicated values of the virus titers being the decadic logarithms of $TCID_{50}/0.1$ ml.

|  | Virus titer | | Residual activity % |
|---|---|---|---|
|  | 10 h/4° C. without AMS | 10 h/60° C. with AMS | |
| Plasminogen preparation | 6.6 | <2.5 | 55 |

EXAMPLE 18

A $C_1$-esterase preparation was prepared according to the technique described by D. H. Bind, J. M. Andrews, F. L. Suddath and R. Spencer, Prot. Biol. Fluids 23 551 (1975), Ed. H. Peeters.

1 l plasma was precipitated with a 50% solution of polyethyleneglycol (PEG) to a final concentration of 5%. The precipitate, after separation by centrifugation, was washed with phosphate-buffered saline solution (ionic strength 0.005) and dissolved in 100 ml 0.5M NaCl. After dialysis against isotonic saline solution containing 1 mmol/l $CaCl_2$, the clotted material was removed. A 4×15 cm column was packed with IgG p-azobenzamidoethylamino Sepharose 6B and equilibrated with isotonic saline solution containing 1 mmol/l $CaCl_2$. This column was charged with the plasma fraction produced as described above and was washed free of proteins with the equilibration buffer. Unspecifically bound proteins were eliminated by washing with borate buffered saline solution containing 1 mmol/l $CaCl_2$.

$C_1$-esterase was eluted with a buffer containing 2.5 mmol/l EDTA. The eluate was dialyzed against a Tris-buffered saline solution and lyophilized. 4.5 g of this bulk powder were dissolved in 10 ml water. 1 ml of the solution contained 13.5 mg protein.

The activity of the enzyme, determined with the chromogenic substrate, pyroglutamyl-Gly-Arg-pNA, was measured amidolytically and amounted to 78.1 nmol $pNA.ml^{-1}.min^{-1}$ (determination method according to "Mikrozirkulation und Prostaglandistoffwechsel", Proceedings of the 25th Congress of the Deutschen Arbeitsgemeinschaft für Blutgerinnungsforschung in München, February 1981, p. 221, Schattauer-Verlag, 1981.

The preparation obtained, which exhibited the indicated properties, was then inoculated with poliomyetlitis virus type I and admixed with 0.8 g ammonium sulfate/ml according to the invention, the pH was adjusted to 7 and it was heated at 60° C. for 10 hours. After the treatment as described, the virus titer and the amidolytic activity were determined. In the following Table the virus titer values and the residual activity in % as compared to an untreated control are indicated, the indicated virus titer values being decadic logarithms of $TCID_{50}/0.1$ ml.

|  | Virus titer | | Residual activity % |
|---|---|---|---|
|  | 10 h/4° C. without AMS | 10 h/60° C. with AMS | |
| $C_1$-esterase preparation | 7.1 | <2.5 | 63 |

What we claim is:

1. A method of inactivating reproducible pathogens in a preparation containing plasmatic enzymes on proenzymes, activated or non-activated coagulation factors, prothrombin complex preparations, plasmatic inhibitors, immunoglobulins or other blood products comprising adding ammonium sulfate to said preparation to attain a salt concentration of more than 0.5 molar, thermally treating said preparation for a period of time sufficient to inactivate the pathogens and removing said ammonium sulfate from said preparation.

2. A method as set forth in claim 1, wherein said preparation has a protein content of from 0.001% to 30%.

3. A method as set forth in claim 1, wherein said preparation having a 2 to 4 molar ammonium sulfate concentration is thermally treated.

4. A method as set forth in claim 1, wherein a protein and ammonium sulfate containing precipitate is recovered from said preparation by adding ammonium sulfate, and said precipitate is thermally treated.

5. A method as set forth in claim 1, wherein said preparation is lyophilized after adding said ammonium sulfate so as to obtain a lyophilisate which is then thermally treated, and an aqueous solvent is added to said thermally treated lyophilisate so as to reconstitute a solution from which said ammonium sulfate is removed.

6. A method as set forth in claim 1, wherein said thermal treatment is carried out during a period of from 1 second to 100 hours and at a temperature of from 40° C. to 121° C.

7. A method as set forth in claim 1, wherein the pH of said preparation during treatment is maintained in a range of from 5 to 11.

8. A method as set forth in claim 7, wherein the pH of said preparation is maintained in a range of from 6.5 to 8.5.

9. A method as set forth in claim 1, wherein protein stabilizing substances are added to said preparation prior to said thermal treatment.

10. A method as set forth in claim 9, wherein said protein stabilizing substance is glycine.

11. A method as set forth in claim 1, wherein antimicrobial substances are added to said preparation prior to said thermal treatment.

12. A method as set forth in claim 11, wherein said antimicrobial substance is caprylate.

13. A method as set forth in claim 1, wherein said removal of ammonium sulfate from said preparation is effected by means of semi-permeable membranes.

14. A method as set forth in claim 1 wherein said activated or non-activated coagulation factors include Factors II, V, VII, VIII, IX, X, XIII and "FEIBA".

15. A method as set forth in claim 1 wherein said other blood products include fibronectin and fibrinogen.

* * * * *

UNITED STATES PATENT AND TRADEMARK OFFICE
CERTIFICATE OF CORRECTION

PATENT NO. : 4,687,664
DATED : Aug. 18, 1987
INVENTOR(S) : Philapitsch et al.

It is certified that error appears in the above-identified patent and that said Letters Patent is hereby corrected as shown below:

Column 2, line 22, "stimultaneously" should read --simultaneously--.

Column 3, line 46, "protein ml" should read --protein/ml--.

Column 5, line 23, "semi-premeable" should read --semi-permeable--.

Column 7, approx. line 47, "clycine" should read --glycine--.

Column 9, line 10, "Acitivity" should read --Activity--.

line 51, "(1979)" should read --(1974)--.

Column 11, line 28, "=" should read --α--.

Column 13, line 16, "Bind" should read --Bing--.

Column 14, line 11, "on" should read --or--.

Signed and Sealed this

Thirteenth Day of March, 1990

Attest:

JEFFREY M. SAMUELS

*Attesting Officer*   Acting Commissioner of Patents and Trademarks